United States Patent
Abbas et al.

(10) Patent No.: US 11,937,897 B2
(45) Date of Patent: *Mar. 26, 2024

(54) OPTICAL OVERLAY DEVICE

(71) Applicants: AI Biomed Corp., Santa Barbara, CA (US); Vanderbilt University, Nashville, TN (US)

(72) Inventors: Adnan Abbas, Santa Barbara, CA (US); Melanie McWade, Nashville, TN (US); Anita Mahadevan-Jansen, Nashville, TN (US)

(73) Assignees: AI Biomed Corp, Santa Barbara, CA (US); Vanderbilt University, Nashville, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/849,074

(22) Filed: Jun. 24, 2022

(65) Prior Publication Data

US 2022/0327799 A1    Oct. 13, 2022

Related U.S. Application Data

(63) Continuation of application No. 17/204,439, filed on Mar. 17, 2021, now Pat. No. 11,403,836, which is a
(Continued)

(51) Int. Cl.
*A61B 5/00* (2006.01)
*A61B 90/00* (2016.01)
(Continued)

(52) U.S. Cl.
CPC .......... *A61B 5/0037* (2013.01); *A61B 5/7445* (2013.01); *A61B 90/361* (2016.02);
(Continued)

(58) Field of Classification Search
CPC .......... A61B 2090/376; A61B 2505/05; A61B 90/36; A61B 5/0037; A61B 5/0064
See application file for complete search history.

(56) References Cited

U.S. PATENT DOCUMENTS

| 7,778,695 B2 | 8/2010 | Black et al. |
| 9,687,190 B2 * | 6/2017 | Mahadevan-Jansen ..................... A61B 5/0086 |

(Continued)

OTHER PUBLICATIONS

Diagnosis and Prognosis of Tissue Pathologies; Microspectroscopy; Manfait et al.—2000. (Year: 2000).*
(Continued)

*Primary Examiner* — Luis Perez-Fuentes
(74) *Attorney, Agent, or Firm* — Carter, DeLuca & Farrell LLP (57) ABSTRACT

Devices and methods for visibly highlighting areas of a region including an imager configured to image the region with a sensitivity to at least one of wavelength, light level, or contrast greater than the human eye, an overlay element configured to visibly highlight areas of the region and registered to the imager to produce alignment of imaged features with highlighted features at the same location on the region, and at least one of a controller executing a program or logic configured to process acquired images from the imager to identify areas of the region determined not visible to the human eye, and control the overlay element to visibly highlight those areas on the region.

20 Claims, 7 Drawing Sheets

Related U.S. Application Data continuation of application No. 16/752,640, filed on Jan. 25, 2020, now abandoned, which is a continuation of application No. 15/043,526, filed on Feb. 13, 2016, now Pat. No. 10,579,891, which is a continuation-in-part of application No. 14/822,447, filed on Aug. 10, 2015, now abandoned.

(51) Int. Cl.
*G06K 9/32* (2006.01)
*G06V 10/145* (2022.01)
*G06V 10/25* (2022.01)

(52) U.S. Cl.
CPC ............ *G06V 10/145* (2022.01); *G06V 10/25* (2022.01); *A61B 5/0071* (2013.01); *A61B 2090/366* (2016.02)

(56) References Cited

U.S. PATENT DOCUMENTS

| | | | |
|---|---|---|---|
| 9,694,198 B2* | 7/2017 | Brown | A61B 18/20 |
| 10,258,275 B2* | 4/2019 | Mahadevan-Jansen | A61B 5/0075 |
| 10,579,891 B2* | 3/2020 | Abbas | A61B 90/361 |
| 11,403,836 B2* | 8/2022 | Abbas | A61B 5/0064 |
| 11,656,180 B2* | 5/2023 | Flanagan | G01N 21/6486 250/459.1 |
| 2002/0044279 A1 | 4/2002 | Khoury | |
| 2002/0105505 A1 | 8/2002 | Sendai | |
| 2002/0177778 A1 | 11/2002 | Averback et al. | |
| 2008/0004533 A1 | 1/2008 | Jansen et al. | |
| 2009/0076380 A1 | 3/2009 | Thierman | |
| 2009/0303317 A1 | 12/2009 | Tesar | |
| 2010/0051808 A1 | 3/2010 | Zeman et al. | |
| 2010/0222673 A1 | 9/2010 | Mangat et al. | |
| 2011/0063427 A1 | 3/2011 | Fengler et al. | |
| 2012/0010483 A1 | 1/2012 | Mahadevan-Jansen et al. | |
| 2012/0268573 A1 | 10/2012 | Schonborn et al. | |
| 2013/0216482 A1 | 8/2013 | Kwon et al. | |
| 2013/0281845 A1 | 10/2013 | Luiken | |
| 2014/0340500 A1 | 11/2014 | Hoegele | |
| 2015/0374452 A1 | 12/2015 | Saito | |
| 2017/0046586 A1 | 2/2017 | Abbas et al. | |
| 2017/0232119 A1 | 8/2017 | Kularatne et al. | |
| 2017/0236022 A1 | 8/2017 | Abbas et al. | |

OTHER PUBLICATIONS

Cell and tissue autofluorescence research and diagnostic appls; Monici et al.—2005. (Year: 2005).*
Raman Spectroscope Study of Different Tissues, Spectroscopy Spectral Analysis, Gang et al. 2005. (Year: 2005).*
Fluorescence-guided minimally invasive parathyroidectomy; Prosst; et al.—2006. (Year: 2006).*
Raman Spectroscopic Study of Different Tissues, Spectroscopy and Spectral Analysis, 2005. Liu Gang et al. (Year: 2005).
Fluorescence-guided minimally invasive parathyroidectomy; vol. 20, p. 1488-1492; 2006. Prosst; et al. (Year: 2006).
Diagnosis and Prognosis of Tissue Pathologies; Microspectroscopy. 2000. Manfait et al., (Year: 2000).
Cell and tissue autofluorescence research and diagnostic appls; vol. 11 pp. 2005. Monici et al. (Year: 2005).
Library USPTO NPL query; 2022 (Year: 2022).
NPL Google Search; 2022. (Year: 2022).
International Search Report and Written Opinion dated Jun. 19, 2020 for corresponding International Application No. PCT/US2020/024510.
Novel optical approach to the interoperative detection of parathyroideal glands; Paras; 2012. (Year: 2012).
Raman Spectroscopic Study of Human Tissues, Spectroscopy and spectral Analysis; Liu et al., 2005. (Year: 2005).
Fluorescence-guided minimally invasive parathyroidectomy; for parathyroid glands, Prosst et al., 2006. (Year: 2006).
NPL internet search Log; 2019. (Year: 2019).
Liu Gang et al., Raman Spectroscopic Study of Different Human Tissues, Spectroscopy and spectral Analysis, vol. 25, No. 5, 723-725, May 2005. (Year: 2005).
Prosst et al.; "Fluorescence-guided minimally invasive parathyroidectomy; a novel detection techynique for parathyroid glands", Surgical Endoscopy and Other techniques, vol. 20, p. 1488-1492; 2006. (Year: 2006).
Manfait et al., Diagnosis and Prognosis of Tissue Pathologies; Microspectroscopy: An Application to Human Thyroid Tumors, Proceedings of SPIE, vol. 3918, 153-160 (May 2000). (Year: 2000).
Monici et al., "Cell and tissue autofluorescence research and diagnostic appls"; vol. 11, pp. 227-256, 2005. (Year: 2005).
Extended Search Report dated Jan. 3, 2017 in European Application No. 2016001764.6.

* cited by examiner

OPTICAL OVERLAY DEVICE

This application is a continuation of U.S. application Ser. No. 17/204,439 filed Mar. 17, 2021; which is a continuation of U.S. application Ser. No. 16/752,640 filed Jan. 25, 2020 (now abandoned); which is a continuation of U.S. application Ser. No. 15/043,526 filed Feb. 13, 2016 (now U.S. Pat. No. 10,579,891) ; which is a continuation in part of U.S. application Ser. No. 14/822,447 filed Aug. 10, 2015 (now abandoned); all of which are incorporated by reference herein.

This invention was made with government support under grant number EB015291 awarded by the National Institutes of Health. The government may have certain rights in the invention.

The specification relates to illuminating a region that has areas not or not easily visible to the human eye and highlighting those areas of the region with a visible light overlay, and in particular for using the capability for surgical applications.

For many processes, including surgical operations, areas of interest in a region may not be visible to the eye of the person performing the process, but may be detectable with an imaging device. For instance, fluorescence can be used to identify areas of a region including areas of surgical interest. Some materials may exhibit fluorescence at non-visible wavelengths. Other areas of interest may exhibit too low a contrast to the human eye to be easily visible. For these situations, which include some parts of the human body, detecting non visible areas of interest and highlighting them visibly may be desirable.

BRIEF DESCRIPTION

In some embodiments, devices and methods may be provided to image a region with a suitable imager capable of detecting areas of interest of the region either not or not easily discernible to the human eye. All or part of the non-visible image scene may be overlaid visibly back onto the imaged region with visible light, to highlight the areas of interest detected from the acquired images.

In some embodiments a device for visibly highlighting areas of a region may be provided including an imager configured to image the region with a sensitivity to at least one of wavelength, light level, or contrast greater than the human eye, an overlay element configured to visibly highlight areas of the region and registered to the imager to produce alignment of imaged features with highlighted features at the same location on the region, and at least one of a controller executing a program or logic configured to process acquired images from the imager to identify areas of the region determined not visible to the human eye, and control the overlay element to visibly highlight those areas on the region.

In some embodiments a method for visibly highlighting areas of a region may be provided including imaging the region with an imager with sensitivity to at least one of wavelength, light level, or contrast greater than the human eye, highlighting visibly areas of the region registered to the imager to produce alignment of imaged features with highlighted features at the same location on the region, and processing acquired images from the imager to identify areas of the region determined not visible to the human eye, and control the illuminator to visibly highlight those areas on the region.

In some embodiments an illuminator configured to illuminate the imaged region may be employed.

In some embodiments the imager may be sensitive to wavelengths outside the visible range.

In some embodiments the illuminator and the imager may both operate at wavelengths outside the visible range.

In some embodiments the illumination may be modulated and the imager may be configured to capture images synchronized to the modulation, allowing for immunity to ambient light.

In some embodiments the imager, illuminator, and overlay element may be configured as one unit at one working distance.

In some embodiments a relationship between the imager and illuminator wavelengths may include being one of different wavelengths, overlapping wavelengths or the same wavelengths.

In some embodiments the highlighting may be configured to be at least one of a single visible color or multiple colors, selected for high contrast with the colors of the region of interest.

In some embodiments the processing may include thresholding the image to highlight the region of interest where the thresholding includes at least one of a predetermined intensity level, predetermined intensity variance, or ratio of intensities at 2 or more locations, 2 or more wavelengths, or at 2 or more locations of full width half max signal.

In some embodiments, the overlay element comprises one or more of a standard light source projector, a laser scanner controlled by the controller to project the visible image by scanning the image on the region, or one or more visible LED's actuated by the controller to scan the image on the region.

BRIEF DESCRIPTION OF THE DRAWINGS

Aspects and advantages of the embodiments provided herein are described with reference to the following detailed description in conjunction with the accompanying drawings. Throughout the drawings, reference numbers may be re-used to indicate correspondence between referenced elements. The drawings are provided to illustrate example embodiments described herein and are not intended to limit the scope of the disclosure.

DETAILED DESCRIPTION OF ILLUSTRATIVE EMBODIMENTS

One or more embodiments described herein may provide for a visible highlighting of features of interest in a region not visible to the eye identified from an images of those features acquired by an imager with more sensitivity to the features than the human eye.

One or more embodiments described herein may provide for visibly highlighting features of the human body for surgery.

One or more embodiments described herein may provide for visibly highlighting features for surgery by imaging areas of interest that fluoresce in a non-visible wavelength and projecting visible highlighting back onto those features.

One or more embodiments may include feature identification and highlighting that is not sensitive to ambient light such as operating room lighting.

Figure 1:
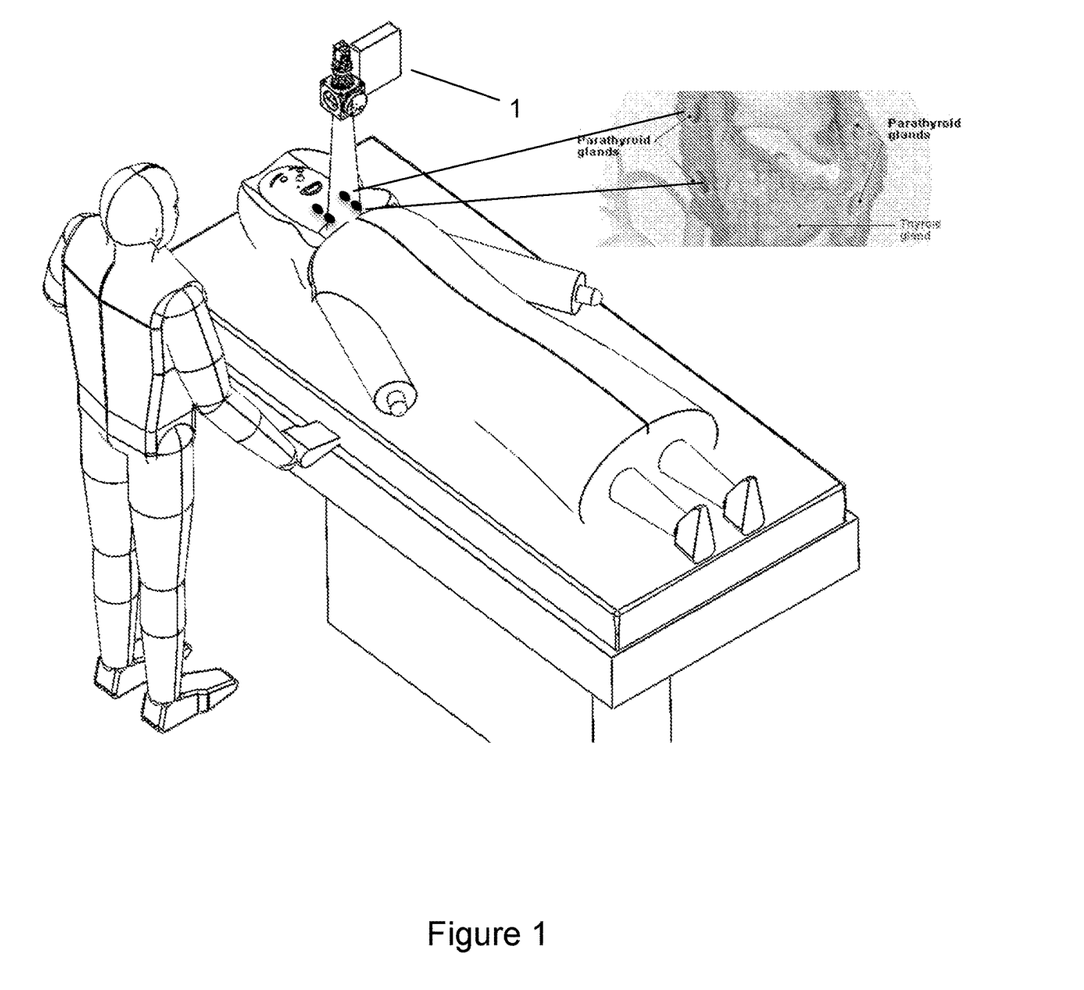
FIG. 1 is an overview of overlay system used in particular medical application according to illustrative embodiments.

Various aspects of the embodiments may include any combination of processing elements and memory that may include computing devices executing software routines, such devices including computers and Personal Electronic Devices, as well as programmable electronics, logic circuits and other electronic implementations. Various combinations of optical elements may be employed including lasers, LED's and other light sources, filters, lenses, mirrors, beamsplitters and the like. The details of the optical, electronic, and processing embodiments described herein are illustrative and are not intended as limiting as alternative approaches using other combinations of like elements may be used to accomplish the same results in essentially the same manner A method for discriminating parathyroid material from thyroid material, using auto-fluorescence, is described in U.S. patent application Ser. No. 13/056,469. This application has inventors in common with the current application, and is incorporated by reference in its entirety. This application discloses that when exposed to radiation in a narrow band about 785 nm, which is just outside visible range, both the thyroid and the parathyroid auto-fluoresce in a wavelength range above 800 nm, also not visible, sometimes centered at 822 nm, and that the parathyroid regions fluorescence intensity is significantly higher than the thyroid regions. This effect can be used to discriminate between the two areas for surgery, for even though the general locations of parathyroid tissue are known, they are hard to discriminate visually accurately enough for surgery, which can be a problem with parathyroid surgery. One detailed embodiment disclosed herein may be applicable to parathyroid surgery. As shown in FIG. 1, an optical overlay device I according to an embodiment of the current disclosure may be used to visibly highlight the parathyroid regions of a patient's exposed internal neck region during surgery. Systems and methods particularly suitable to fluorescence application such as the parathyroid example are described in commonly owned U.S. application Ser. No. 14/822,477, filed Aug. 10, 2015, which is incorporated by reference in its entirety.

The parathyroid application is an example of a process where an operator, in the parathyroid case, a surgeon, needs to perform a process on areas of interest in a region where he may not be able to see the areas of interest by eye. In the case of the parathyroid example, the fluorescing parathyroid material is fluorescing in the near infrared. However in general, imagers of various types can be made that exceed the eye's sensitivity not just in terms of detectable wavelengths, but also in terms of contrast or low light sensitivity.

Figure 2:
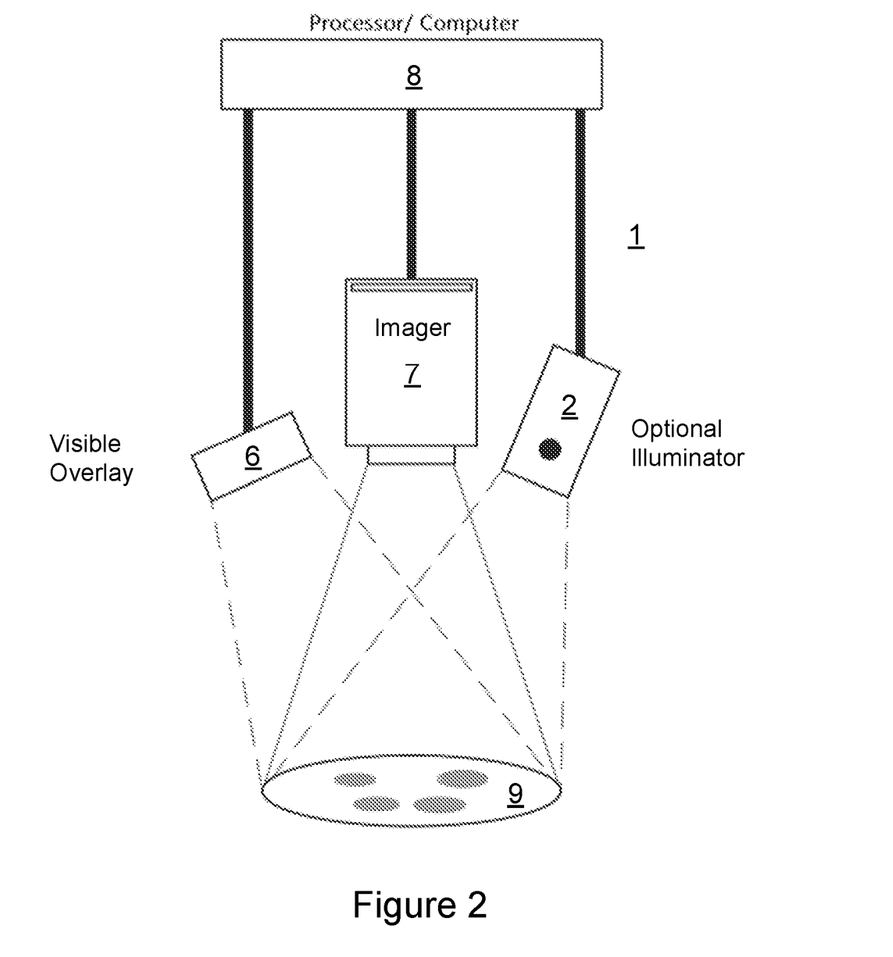
FIG. 2 is a block diagram of an general illustrative device embodiment.

FIG. 2 illustrates a general embodiment of a system 1 for overlaying visible highlighting onto non-visible areas 9 of interest in a region. Optionally the region may be illuminated by an illuminator 2. For the case of fluorescence, this illuminator may be selected to operate at a wavelength which will stimulate the desired fluorescing behavior. Or the illuminator could be a visible light source, such as an operating table light or other workstation lighting device. It could be a UV light, or another EM radiation source, Not all applications will require the illuminator. Imager 7 is selected to be sensitive to the characteristics of the area of interest, and may be an IR imager, a UV imager, an X-ray imager, other electromagnetic imager, a low light visible imager, or a visible imager configured either in hardware or with signal processing for high contrast imaging. The imager of whatever type should be able to detectably image features the operator cannot see by eye. The imager and optional illuminator may either or both operate at non-visible wavelengths, and the imager and optional illuminator may or may not overlap in operating wavelength. Processor 8 receives the images acquired by imager 7 and processes the images to identify the areas of interest by filtering or processing of various types, Filtering may include, high/low intensity, deviation from average, within a range, near predetermined locations, or any combination thereof, or other filtering/processing techniques, The processing may include thresholding the image to highlight the region of interest where the thresholding includes at least one of a predetermined intensity level, predetermined intensity variance, or ratio of intensities at 2 locations on the region, the ratio of 2 wavelengths, or the ratio data representative of the full width half max of signal at two or more locations, wavelengths or the like. Other processing techniques for feature identification may be suitable. The desired result is identification locations on the imaged region likely to be the material of interest. The processor then controls an overlay element 6 to highlight the areas 9 identified by the filtering on the region with visible light highlighting visible to the operator. The overlay element and imager are registered to the working region by mechanical, optical, image processing or some combination of techniques. For embodiments where the imager, overlay element and optional illuminator are configured as one or more units all at one working distance, such registration is straightforward.

A variety of overlay techniques could be employed in various embodiments. A standard light source projector could be used with suitable optics. Other embodiments could use a scanning laser as used in Laser show devices, and other illumination applications, by inputting the signal from the camera a 7 and programming the projector laser 6 output to accurately illuminate specific areas corresponding areas of interest. Other embodiments could employ 1 or more, and up to 4 or more LEDs/Lasers that are controlled by X and Y axis motors (possibly with the laser at a hinge point) to accomplish the same result as a laser scanner. For this embodiment, programming the motor movements to illuminate a specific point with the laser may indicate where the areas of interest lies. For the parathyroid case, there are four parathyroids, the system could either quickly move the motors of one LED/Laser to illuminate multiple areas with sufficient refresh rate or could control up to 4 LEDs/Lasers to independently accomplish that same function. The visible overlay color may be single color or multi-color and chosen to contrast with the background. For instance for surgical operations, a green overlay color contrasts well with the predominantly red background.

Figure 3:
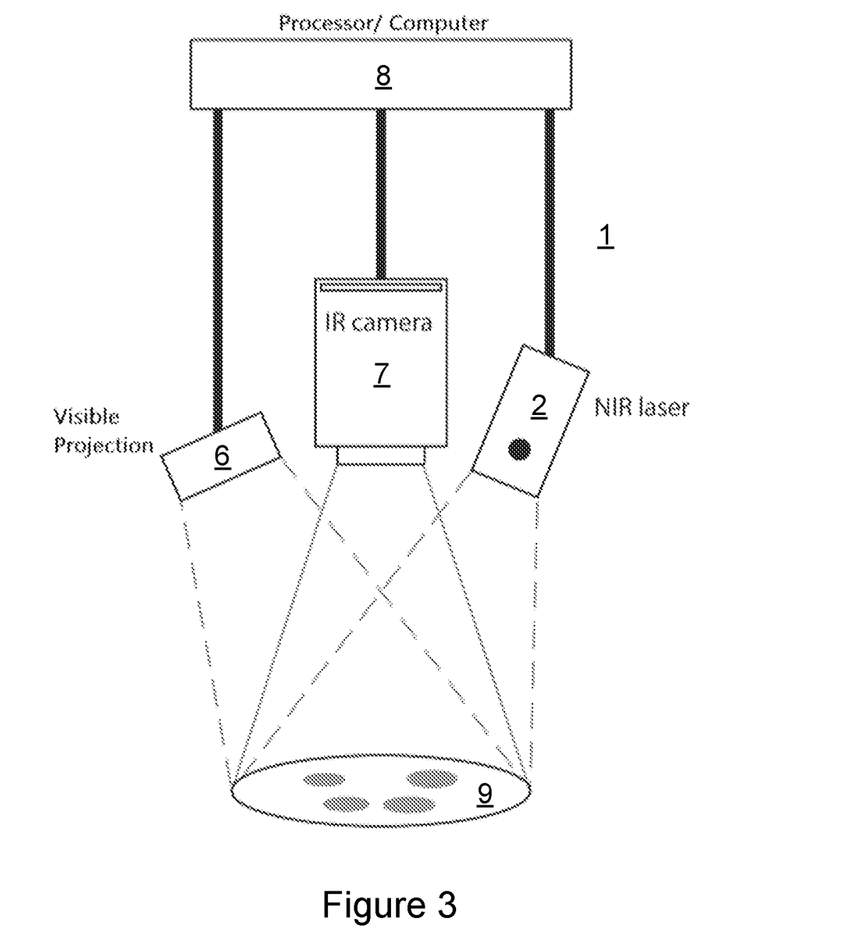
FIG. 3 is a block diagram of another general illustrative device embodiment.

FIG. 3 illustrates the case where the illumination 2 is in the near IR, the imager 7 is an IR camera and the overlay element 6 is a visible projector. This is useful for cases such as the parathyroid where areas of interest either fluoresce or are otherwise more visible in the ir. For many surgical applications the working region containing the areas of interest is usually less than 10 cm in the longest direction.

Figure 4:
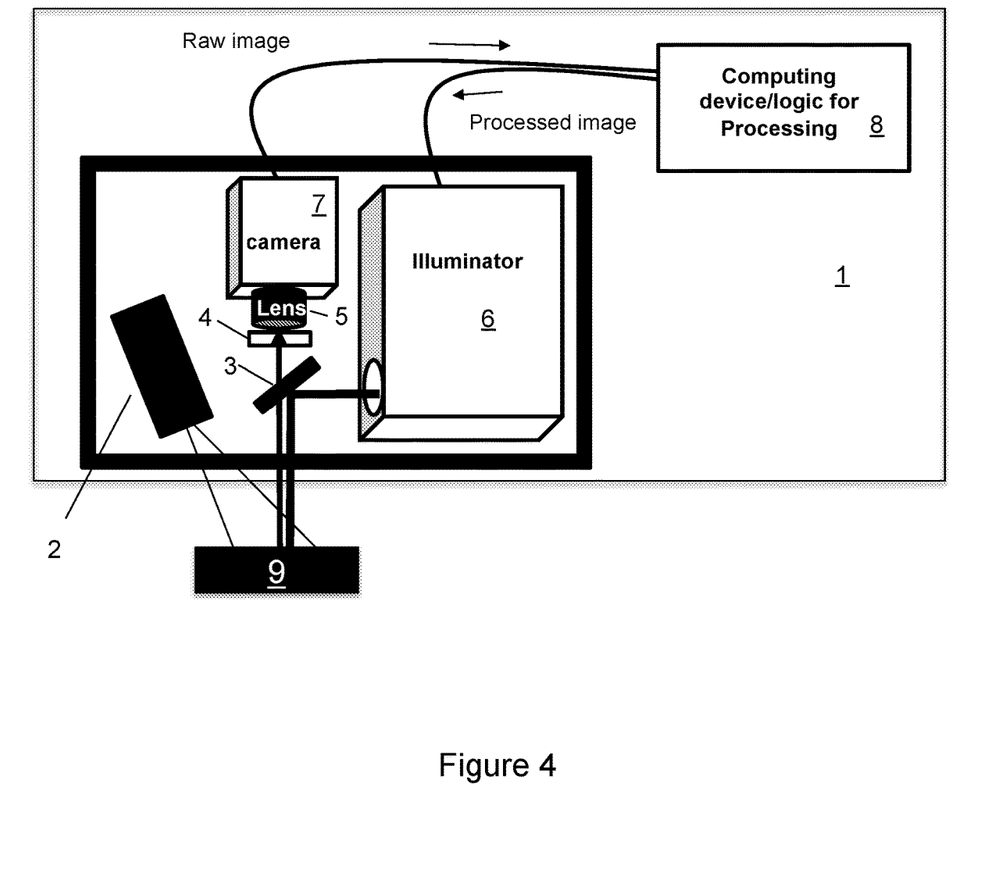
FIG. 4 is a block diagram of a more detailed illustrative device embodiment.

FIG. 4 shows a more detailed illustrative device embodiment for the IR fluorescence overlay 1. Light source 2 at a first wavelength bandwidth illuminates a region of interest 9.

The first wavelength bandwidth is used to stimulate emissions or fluorescence at a second wavelength bandwidth, which may be different from the first, expected from areas to be identified of the region of interest. Those emission wavelengths are not visible for applications utilizing the device. An optional filter 4 may be used to pass wavelengths within the emission bandwidth and block others. An optional lens may be used 5 to set working distance of the device. Camera 7 is chosen to be capable of imaging the emission wavelength bandwidth or at least the portion passed through the filter 4. The image is acquired by computing device/logic 8 which also controls a visible light projector 6. Controllable Projector 6 and camera 7 are registered such that the imaged area and the projected area are aligned both in orientation and size so that features in the camera image or any portion of the camera image project back down on the region 9 such that their visible projection aligns precisely onto the actual physical features. The registration may be accomplished through optical design, which may be improved using calibration regions with definable edges and programming the projector to match such calibration pieces at a desired working distance for actual operation. Such edge or other feature detection may be updated in actual use by observing and correlating image features in actual regions of interest. The projection may be made co-linear with the imaging axis by use of a partially reflective element 3, such as a beamsplitter. Obviously different optical arrangements, such as which elements are on or off axis, may be accomplished with different arrangements of optical elements and still function as described for the illustrative arrangement of FIG. 4.

Figure 5:
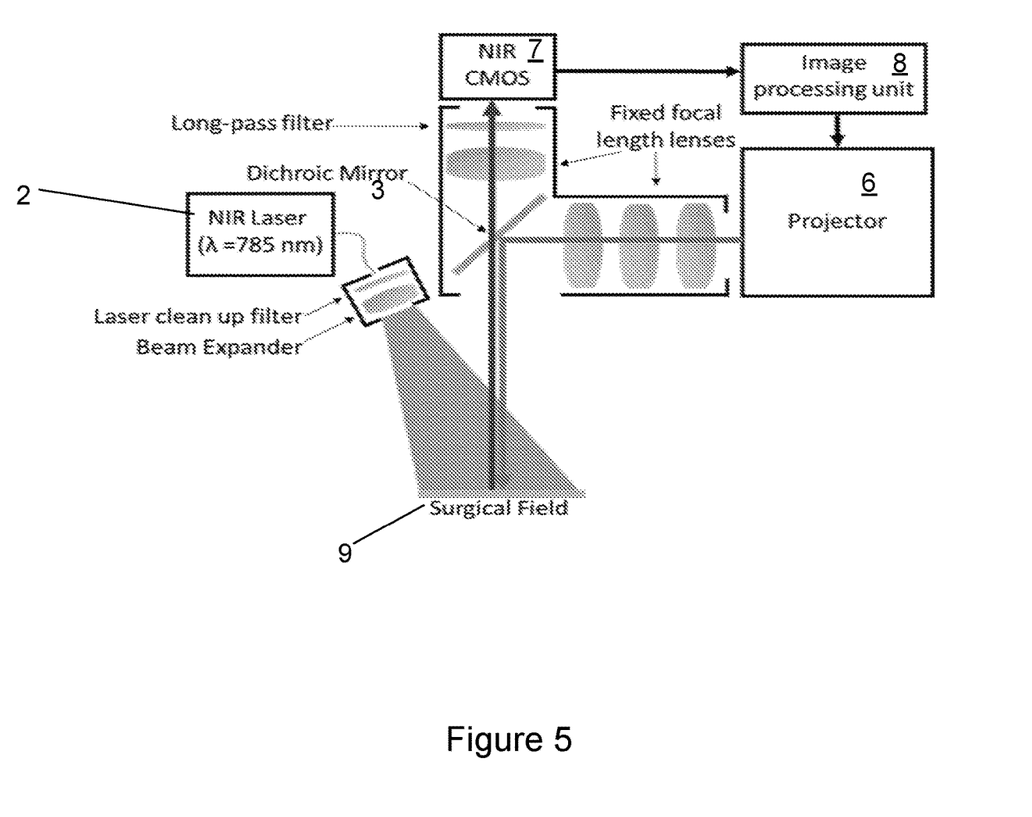
FIG. 5 is a block diagram of a specific illustrative device embodiment.

In FIG. 5 a specific embodiment aimed at the parathyroid surgical application is Acquisition parameters needed for clinical use, suggest an exemplary set of design criteria for an overlay device–Spot size=5 cm diameter, Image size=5×7 cm, Lateral resolution=500 microns, SNR=4 (for laser power density=7 mW), Image acquisition time=100 ms.

Figure 6:
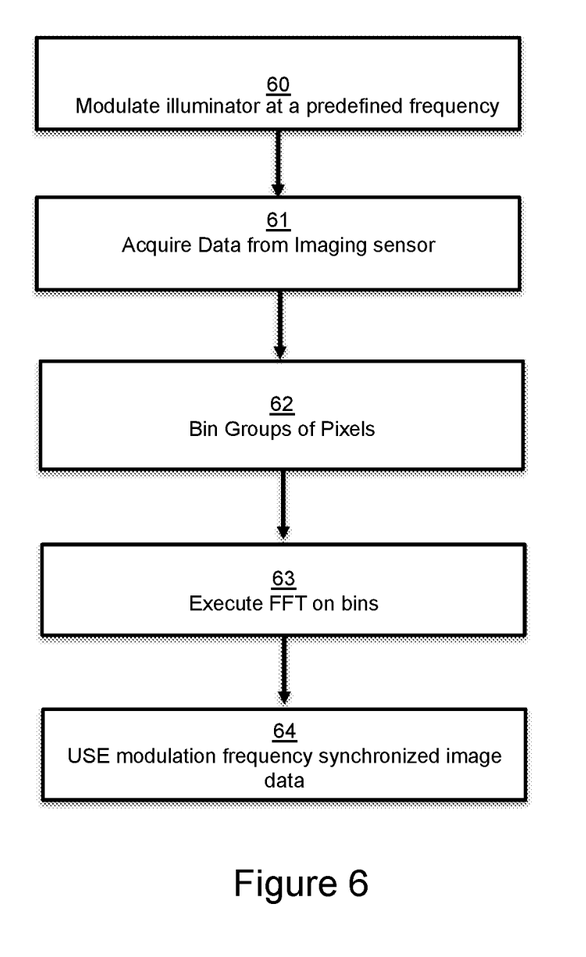
FIG. 6 is a flowchart of a illumination synchronization process according to an illustrative embodiment

For the parathyroid surgical overlay device of FIG. 6 a projector-based 6 system is employed to enhance visualization by overlaying NIR autofluorescence structures with visible light in real-time. The surgical field 9 is illuminated with a near-infrared (NIR) diode laser 2 ($\lambda$=785 nm, Innovative Photonics Solutions) coupled through a 400-μm fiber optic patch cable, filtered with a laser clean-up filter (Semrock), and focused with a plano-convex lens (f=75 mm, Thorlabs) to achieve a 5-cm diameter spot size. The emitted NIR autofluorescence is filtered through a long-pass filter (800-nm, Semrock) to eliminate the elastically scattered light and specular reflectance and detected using a NIR CMOS camera 7 (Basler AG). The raw NIR image is sent to a processor including an image processing unit 8 for real-time image processing. The processed image is then be sent to a high-lumen light-emitting diode (LED) projector 6 (AAXA Technologies), which projects the false colored image through a dichroic filter/mirror 3 (801-nm, Semrock) and on to the surgical field 9.

A software program is used for real-time processing of the NIR fluorescence images. Images collected by the NIR camera is sent to the processor. Exemplary Image Processing/filtering includes initially subtracting a dark frame. The image is sent through a convolution filter and a feature extraction algorithm to achieve morphological transformation. This series of steps achieves maximal signal intensity in the areas of low level fluorescence present in the surgical field. The processed image is sent to the projector and converted to a green color intensity before projection on the tissue. The software also allows co-registration of the projected image with real space using a series of x and y manipulation controls. Image coregistration may be performed prior to each imaging event using a fluorescent grid phantom as a registration target.

Spatial resolution of the parathyroid overlay system of FIG. 5 should be able to resolve features as small as 3 mm parathyroid glands. The system should be capable of detecting fluorescence with 30 mW excitation at 785 nm thus qualifying for class 3R medical device status.

NIR illumination/excitation in the 30 mW range may be accomplished with a laser, However the use of lasers may complicate meeting FDA regulations for application such as operating room equipment and also may the flexibility of use in the operating room (i.e. requiring a foot switch to activate the laser). LEDs excitation sources set to the same wavelength and similar power may be suitable and in some cases desirable alternatives. A LED based device tested using LEDs from Epitex (SMBB780D-1100-02) has shown the ability of the LED(s) to produce enough radiant power to a parathyroid surgical site at a working distance of 500 mm away from the surgical to detect the fluorescence signals from parathyroid and thyroid, The performance of such a system may be comparable with a diode laser based device and may have advantages as described above. A decision will be made at this point about whether to continue using a laser or to switch to using LEDs. An LED illuminator may be realized as a series of LEDs at the annular opening around an imager camera lens so as to increase the radiant output as well as to eliminate or reduce any shadowing effect that is cause when using one LED and working with a surgical site that isn't flat.

It is desirable for many applications to be able to operate the overlay system in whatever suitable ambient lighting exists. For instance, surgical operating rooms often include bright light sources that may interfere with the overlay device, particularly when the wavelengths of interest are NIR. It may be inconvenient however to turn off ambient lighting. For example, for a surgical application;

a. The surgeon and staff cannot adequately see if some or all lights are off
 b. Even if most lights are off during signal acquisition, sources of light such as indicator lights, monitors etc. may still leak through. The leaked light main spectral components in the same spectral range as the wavelengths of interest. This results in decreased signal-to-noise ratio and decreases the parathyroid detection sensitivity.

To use the overlay system with ambient lighting on, it may be desirable to employ modulated illumination to synchronize image acquisition with the modulation characteristic. For example, a simulated lock-in/Fast Fourier Transfer (FFT) with an imaging sensor to eliminate light leakage into the sensor is one approach. This light leakage can result in high ambient noise levels that can exceed the output from detected features, for example autofluorescence. By utilizing the process described below, the fluorescence signal intensity will remain visible while eliminating any other light that can leak into the sensor without having to dim the ambient lighting such as Operating Room (OR) lights. The illumination/excitation light (laser or LED or similar) is modulated by pulsing at a frequency that is distinct from those of the ambient lighting. The resulting features of interest will emit at that same frequency. As such, by taking the FFT of the acquired image, the desired output (such as from autofluorescence) can be differentiated from any other light. FIG. 6 is a flow chart of an illustrative process. In step 60, the illuminator is modulated at a predetermined frequency. In step 61 image data is acquired from a sensor. In step 62 groups of pixels are sorted into bins. In step 62 a Fast Fourier Transform (FFT) is executed on the bins. In step 64, modulation frequency synchronized image data is used to develop overlaying An alternative approach to the use of FFT is to acquire a diffuse reflectance image with ambient lights on and illuminator off. This image can then be used to subtract the background and along with image processing can be used to obtain a high-contrast fluorescence image with the light on. Electronic lock-in approaches may also be suitable. Another alternative embodiment may use image detection technology that utilizes a Gabor filter, which is used for edge detection. Frequency and orientation representations of Gabor filters are similar to those of the human visual system, and they have been found to be particularly appropriate for texture representation and discrimination. In the spatial domain, a 2D Gabor filter is a Gaussian kernel function modulated by a sinusoidal plane wave. Another embodiment may include specific lighting (with defined wavelength) that is part of the camera system chosen to lessen the detrimental external lighting effects on the overlay system. This lighting may be cropped out using the filters in front of the camera, or may source from a limited bandwidth illuminator such as specific LED's or laser illuminators. Thus the OR lights may be turned off with exception of these specific lights that are provided with the camera system to illuminate the desired region.

Figure 7:
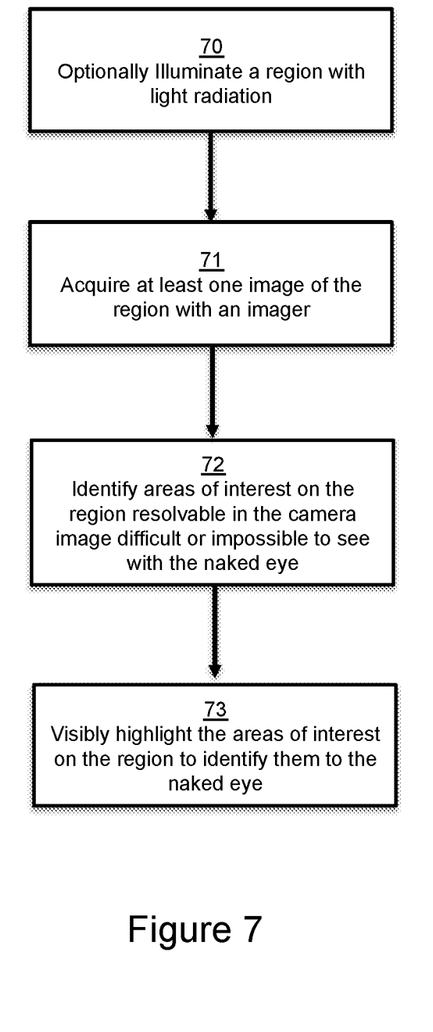
FIG. 7 is flow chart of a method according to an illustrative embodiment.

FIG. 7 is a flow chart of a method of operating a general overlay device such as the one shown in FIG. 2 for a case where a non—visible fluorescence of a material of interest may be used to identify the locations of that material in a region. In step 70 a region is optionally illuminated with electromagnetic radiation, which may be any of a variety of types, UV, bright visible, low intensity visible, X-Ray, other EM radiation, narrowband, at a wavelength chosen to excite a desired non-visible fluorescence of a material of interest, or any type chosen to aid in identifying features not discernible by eye. In step 71 one or more images are acquired in a bandwidth that is useful for detecting areas of interest. In step 72 the image is filtered to select identify the non-visible areas of interest. Filtering may include, high/low intensity, deviation from average, within a range, near predetermined locations, or any combination thereof, or other filtering/processing techniques. The desired result is identifying locations likely to be the material of interest. In step 73, the overlay element is controlled to highlight all or part of the acquired image, which may be just of the selected locations, back onto the region with visible light. This will have the effect of illuminating the selected locations 9 on the region with visible highlighting.

The embodiments described herein are exemplary. Modifications, rearrangements, substitute devices, processes etc. may be made to these embodiments and still be encompassed within the teachings set forth herein.

The invention claimed is:

1. A system for distinguishing between different tissues during surgery, the system comprising:
   an emitter configured to direct radiation at a pre-determined wavelength toward a region of a patient to illuminate and stimulate at least first and second tissues of the region of the patient;
   an imager configured to collect radiation corresponding to the autofluorescence of the first and second tissues having wavelengths above a pre-determined wavelength threshold;
   at least one processor for processing images from the imager, the at least one processor configured to distinguish between the radiation from the autofluorescence of the first tissue and the radiation from the autofluorescence of the second tissue based on autofluorescence intensity; and
   an overlay device controlled by the at least one processor, the overlay device configured to visibly highlight, in the region of the patient, areas of the autofluorescence of the first tissue.

2. The system according to claim 1, wherein the emitter is a UV light emitter.

3. The system according to claim 1, wherein the overlay device is configured to visibly highlight areas of the autofluorescence of the first tissue as small as 3 mm.

4. The system according to claim 1, wherein the overlay device includes a laser scanner controlled by the at least one processor to visibly highlight the areas of the autofluorescence of the first tissue.

5. The system according to claim 1, wherein the overlay device includes at least one LED or at least one laser controlled by the at least one processor to visibly highlight the areas of the autofluorescence of the first tissue.

6. The system according to claim 5, further comprising X and Y axis motors controlled by the at least one processor for controlling an orientation direction of the at least one LED or the at least one laser.

7. The system according to claim 1, wherein the illumination by the emitter is modulated, and wherein the imager is configured to capture images synchronized to the modulation allowing for immunity of the imager to ambient light.

8. The system according to claim 7, wherein synchronization of the imager to the modulation eliminates adverse effects of light leakage.

9. The system according to claim 1, wherein the emitter, the imager, and the overlay device are configured as one unit configured for positioning a working distance from the region of the patient.

10. The system according to claim 1, wherein the visibly highlighted areas are visibly highlighted by the overlay device with at least one color selected for high contrast with of the region of the patient.

11. A method for distinguishing between different tissues during surgery, the method comprising:
   directing radiation having a pre-determined wavelength toward a portion of a patient to illuminate and stimulate at least first and second tissues of the region of the patient into autofluorescence;
   collecting radiation corresponding to the autofluorescence of the first tissue and the autofluorescence of the second tissue having wavelengths above a pre-determined wavelength threshold;
   distinguishing between the radiation from the autofluorescence of the first tissue and the autofluorescence of the second tissue based on autofluorescence intensity; and
   visibly highlighting, in the region of the patient, areas of the autofluorescence of the first tissue.

12. The method according to claim 11, wherein the directing radiation includes directing radiation from a UV light emitter.

13. The method according to claim 11, wherein the visibly highlighting includes visibly highlighting areas of the autofluorescence of the first tissue as small as 3 mm.

14. The method according to claim 11, wherein the visibly highlighting includes laser scanning the areas of the autofluorescence of the first tissue.

15. The method according to claim 11, wherein the visibly highlighting includes directing at least one LED or at least one laser towards the areas of the autofluorescence of the first tissue.

16. The method according to claim 15, wherein the visibly highlighting includes controlling X and Y axis motors to thereby control an orientation direction of the at least one LED or the at least one laser.

17. The method according to claim 11, wherein the directing radiating includes modulating the radiation, and wherein the collecting radiation includes capturing images synchronized to the modulation allowing for immunity of the collecting radiation to ambient light.

18. The method according claim 11, wherein the directing radiation, the collecting radiation, and the visibly highlighting are performed by one unit positioned a working distance from the region of the patient.

19. The method according to claim 11, wherein the visibly highlighting includes visibly highlighting with at least one color selected for high contrast with the region of the patient.

20. The method according to claim 11, wherein the region of the patient includes the neck of the patient.

* * * * *

UNITED STATES PATENT AND TRADEMARK OFFICE
CERTIFICATE OF CORRECTION

PATENT NO. : 11,937,897 B2
APPLICATION NO. : 17/849074
DATED : March 26, 2024
INVENTOR(S) : Adnan Abbas, Melanie McWade and Anita Mahadevan-Jansen Page 1 of 1

It is certified that error appears in the above-identified patent and that said Letters Patent is hereby corrected as shown below:

In the Specification

At Column 1, Line 14, please delete "may have" and replace it with "has".

Signed and Sealed this
Twenty-first Day of October, 2025

John A. Squires
*Director of the United States Patent and Trademark Office*